US012357869B2

(12) United States Patent
Huang et al.

(10) Patent No.: US 12,357,869 B2
(45) Date of Patent: Jul. 15, 2025

(54) METHOD, EXERCISE DEVICE AND SOFTWARE FOR MEASURING MAXIMUM MUSCLE STRENGTH VALUE

(71) Applicant: ESound Technology Co., Ltd., Taipei (TW)

(72) Inventors: Yung Hui Huang, Taipei (TW); TingChun Su, Taipei (TW)

(73) Assignee: ESound Technology Co., Ltd., Taipei (TW)

( * ) Notice: Subject to any disclaimer, the term of this patent is extended or adjusted under 35 U.S.C. 154(b) by 0 days.

(21) Appl. No.: 18/662,235

(22) Filed: May 13, 2024

(65) Prior Publication Data

US 2024/0382799 A1     Nov. 21, 2024

(30) Foreign Application Priority Data

May 21, 2023 (TW) ................. 112118835

(51) Int. Cl.
*A63B 21/00* (2006.01)
*A61B 5/22* (2006.01)
*A63B 24/00* (2006.01)

(52) U.S. Cl.
CPC .......... *A63B 21/40* (2015.10); *A61B 5/224* (2013.01); *A63B 24/0062* (2013.01); *A63B 2024/0065* (2013.01); *A63B 2230/605* (2013.01)

(58) Field of Classification Search
CPC ............. A63B 21/40; A63B 24/0062; A63B 2024/0065; A63B 2230/605; A61B 5/224; A61B 5/227
See application file for complete search history.

(56) References Cited

U.S. PATENT DOCUMENTS

| 10,688,343 | B2 * | 6/2020 | Su ..................... A63B 24/0062 |
| 2021/0197023 | A1 * | 7/2021 | Liang ................ A63B 24/0087 |

FOREIGN PATENT DOCUMENTS

| EP | 3469987 | A1 * | 4/2019 | ............ A61B 5/221 |
| JP | 3948617 | B2 * | 7/2007 | .......... A61B 5/0537 |
| JP | 2014061084 | A | 4/2014 | |
| JP | 2017209519 | A | 11/2017 | |
| KR | 20090090842 | A * | 8/2009 | |

(Continued)

*Primary Examiner* — Octavia Hollington
(74) *Attorney, Agent, or Firm* — Schmeiser, Olsen & Watts LLP

(57) ABSTRACT

The invention relates to a method, an exercise device and a software for measuring maximum muscle strength value. Wherein, the method for measuring the maximum muscle strength value through an exercise device with dynamically variable resistance signal-connected to an arithmetic control unit, is obtained by performing the following steps. The steps include: an obtaining original muscle strength value step, an initial muscle strength value generation step and a maximum muscle strength value generation step. The characteristic of the present invention is that the maximum muscle strength value is obtained according to the position of the exercise process, which overcomes the shortcoming of traditional technology that can only obtain a single data. Moreover, the present invention further forms a maximum muscle strength curve, whereby the obtained data can be used in fitness training to effectively improve training effects and avoid muscle injuries caused by overloading.

2 Claims, 3 Drawing Sheets

(56) References Cited

FOREIGN PATENT DOCUMENTS

| | | | | |
|---|---|---|---|---|
| KR | 20090119514 | A | * | 11/2009 |
| KR | 101979393 | B1 | * | 5/2019 |
| KR | 20200119991 | A | * | 10/2020 |
| KR | 102244687 | B1 | * | 4/2021 |
| TW | 201914527 | A | | 4/2019 |
| TW | 202033243 | A | | 9/2020 |

* cited by examiner

METHOD, EXERCISE DEVICE AND SOFTWARE FOR MEASURING MAXIMUM MUSCLE STRENGTH VALUE

CROSS-REFERENCE TO RELATED APPLICATION

This non-provisional application claims priority under 35 U.S.C. § 119(a) to Patent Application No. 112118835 filed in Taiwan, R.O.C. on May 21, 2023, the entire contents of which are hereby incorporated by reference.

BACKGROUND

Technical Field

The present invention is a method, device and software for measuring a user's maximum muscle strength value, particularly a method, device and software achieved through exercise equipment with a variable resistance system.

Related Art

When generally exercising, in order to be able to grasp your own condition, you usually understand it through some numerical conditions, wherein the maximum muscle strength is one of them. By understanding your own maximum muscle strength, you can arrange your own training progress, confirm whether the training plan is effective, and help adjust training intensity and plan to achieve better results.

When the human body is exercising, it relies on the contraction of muscles to generate force. However, experiments have shown that during the entire contraction process of the muscles, the generated force is dynamically changed and it does not continue to be a certain value. There are two traditional muscle strength testing methods, namely: (1) During the exercise course, the maximum strength is tested repeatedly that the muscles can be withstood by gradually increasing a single weight. Full rest and warm-up are required before each testing. The final completion of the exercise represents the maximum force that the muscle can produce when contracting. (2) Repeat the exercise several times with a lighter fixed weight until the user is exhausted and unable to continue, and then use the formula to calculate the maximum muscle strength value. However, the maximum muscle strength value obtained by these two methods is only a single value and cannot show the actual force changes of the muscle throughout the contraction process. Therefore, the proposed training course may be too light or too heavy at a certain position in the exercise process. This can lead to ineffective training or muscle injuries.

SUMMARY

In view of the above problems, the inventor of the present invention provides a method that can measure the maximum muscle strength value. The maximum muscle strength value obtained by this method is obtained along with the position of the exercise process. Therefore, it overcomes the shortcomings of traditional technology that can only obtain single data. When the data obtained by this method is used in fitness training, it can effectively improve the training effect and avoid muscle injuries caused by overloading.

A method for measuring the maximum muscle strength value of the present invention, which through an exercise device with dynamically variable resistance and an arithmetic control unit connected with its signal, performs the following steps: an obtaining original muscle strength value step, an initial muscle strength value generation step and a maximum muscle strength value generation step. Wherein, the obtaining original muscle strength value step is that a user performs at least one exercise process at a constant speed on the exercise device with dynamically variable resistance, and records the force value exerted by the user at each position in the exercise process, and defines the force value exerted as the original muscle strength value. The initial muscle strength value generation step enables the arithmetic control unit to increase, decrease or remain unchanged according to the original muscle strength value of each position to generate an initial muscle strength value for each position. The maximum muscle strength value generation step means that after receiving the initial muscle strength value, the exercise device with dynamically variable resistance performs an exercise test, and during the exercise test, each initial muscle strength value is gradually increased, and the initial muscle strength value is defined after being increased as a test muscle strength value; after completing the specified conditions of the exercise test, the highest test muscle strength value achieved at each position during the exercise test is the maximum muscle strength value at that position. In the embodiment of the present invention, the specified condition is to start the exercise test with the initial muscle strength value, and after each exercise process or several exercise processes, the tested muscle strength value is increased at each position by a certain value or an equal proportion.

The present invention further provides a method for measuring the maximum muscle strength value, which through an exercise device with dynamically variable resistance and an arithmetic control unit connected with its signal, performs the following steps: an obtaining the original muscle strength value step, an initial muscle strength value generation step and a maximum muscle strength value generation step, and records the force value exerted by the user at each position in the exercise process, and the force value exerted is defined as the original muscle strength value. The initial muscle strength value generation step is that the arithmetic control unit can increase, decrease or remain unchanged according to the original muscle strength value of each position to generate an initial muscle strength value for each position. The maximum muscle strength value generation step is that the exercise device with dynamically variable resistance performs an exercise test after receiving the initial muscle strength value. During the exercise test, a test muscle strength value greater than or equal to the initial muscle strength value is used; after completing the specified conditions of the exercise test, the maximum muscle strength value is obtained according to a conversion formula. In the embodiment of the present invention, the specified condition may also be to perform a plurality of exercise processes with a certain initial muscle strength value, and there may be no rest between each exercise process until the user no longer performs it. The maximum muscle strength value is equal to $W_1/(1+(1-Y) \times c)$ when the accumulated number of exercise processes are no longer performed. $Y$ is the accumulated number of exercise processes before the user no longer performs the action, $W_1$ is the certain initial muscle strength value, and $c$ is a constant and between 0.01-0.1.

The present invention further provides a method for measuring the maximum muscle strength value, which through an exercise device with dynamically variable resistance and an arithmetic control unit connected with its signal, performs the following steps: an obtaining the original muscle strength value step, an initial muscle strength value generation step and a maximum muscle strength value generation step. Wherein, the obtaining the original muscle strength value step is that a user performs at least one exercise process at a constant speed on the exercise device with dynamically variable resistance, and records the force value exerted by the user at each position in the exercise process, and defines the force value exerted as the original muscle strength value. The initial muscle strength value generation step is that the arithmetic control unit can increase, decrease or remain unchanged according to the original muscle strength value of each position to generate an initial muscle strength value for each position. The maximum muscle strength value generation step is that the exercise device with dynamically variable resistance performs an exercise test after receiving the initial muscle strength value. During the exercise test, a plurality of test muscle strength values greater than or equal to the initial muscle strength value are used; after completing the specified conditions of the exercise test, the maximum muscle strength value is obtained according to a conversion formula. In the embodiment of the present invention, the specified condition is to start the exercise test with the initial muscle strength value, and in each exercise process, the test muscle strength value at each position by a certain value or an equal proportion is increased, at this time, the conversion formula for the maximum muscle strength value at each position is:

$$W_1/(1+(1-n)\times c)+(W_2-W_1)/(1+(1-n+1)\times c)+$$
$$\ldots (W_n-W_{n-1})/(1+(1-n+n-1)\times c)$$

Wherein, $W_1$ is the muscle strength value of the first test, $W_2$ refers to the muscle strength value of the second test, $W_n$ refers to the muscle strength value of the nth test, c is a constant and between 0.01-0.1.

By the aforementioned method, the maximum muscle strength value can be obtained, that is, the maximum muscle strength value at each position in the exercise process, which is not the conventional maximum value in the entire exercise process, and the maximum muscle strength value obtained through the present invention can be used as a reference value for dynamic adjustment during training, which has the effect of improving the training effect.

Further, the present invention can use the arithmetic control unit to draw a line according to the maximum muscle strength values at each exercise process position, thereby generating a maximum muscle strength curve.

In the embodiment of the present invention, the increased manner of the initial muscle strength value is to increase the test muscle strength value in an equal proportion, an equal difference, a certain value or non-linear manner at each position of the exercise process.

The present invention further provides an exercise device for measuring maximum muscle strength value, which includes: an exercise unit, a dynamically adjusted resistance unit and an arithmetic control unit. The exercise unit is used for the user to perform at least one exercise process. The dynamically adjusted resistance unit is used to control the resistance during each exercise process. The arithmetic control unit is signal-connected to the exercise unit and the dynamically adjusted resistance unit to execute the aforementioned method to calculate the maximum muscle strength value. In addition to calculating maximum muscle strength, this device can also correspond to the output control of the dynamically adjusted resistance unit for the user using in fitness training.

The present invention further provides a kind of software for measuring the maximum muscle strength value, which can be installed in an arithmetic control unit. The arithmetic control unit is signal-connected to an exercise device with dynamically variable resistance. After executing the aforementioned method, the maximum muscle strength value is obtained. The maximum muscle strength value obtained can also be transmitted to the arithmetic control unit to control the exercise device with dynamically variable resistance, corresponding to the maximum muscle strength curve, and outputting resistance according to the position, providing the user with a better fitness experience.

DETAILED DESCRIPTION

The embodiment of the present invention is a method for measuring the maximum muscle strength value, which can obtain the maximum muscle strength value at each position within the range of exercise process, whereby it can be used as basic information for training muscle strength increased, and protects the user from muscle injuries. In the following, the device of this embodiment and the method of this embodiment will be used for description. Furthermore, in the embodiment of the present invention, each exercise process is taken as a unit, that is, the data composed of each process is viewed as a whole. Although the calculation is performed based on the position, it still belongs to the data within the process. Therefore, embodiments of the present invention can also use the two-dimensional data formed by the position and force of each exercise process to form a curve for the user observing and interpreting.

Figure 1:
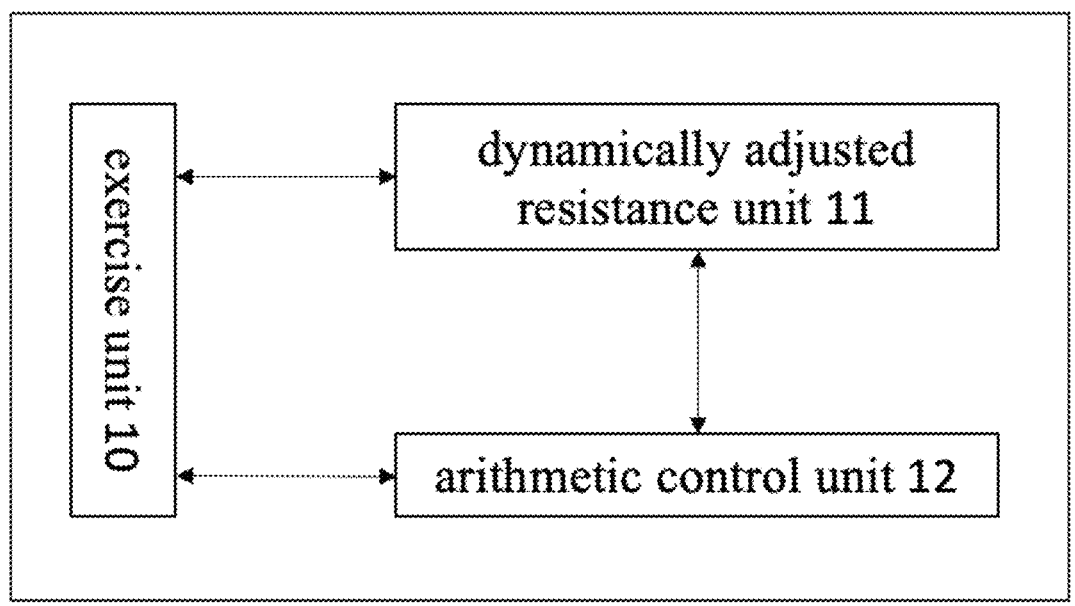
FIG. 1 is a schematic diagram of an exercise device according to an embodiment of the present invention.
Figure 2:
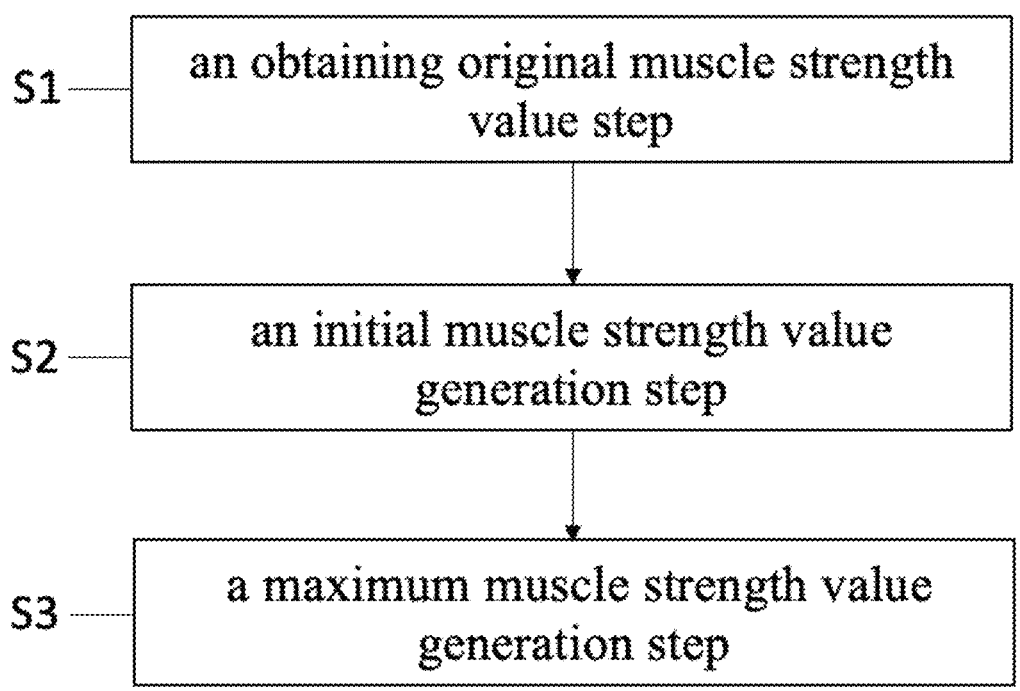
FIG. 2 is a flow chart of an embodiment of the present invention.

Please refer to FIG. 1, the device of this embodiment includes the invention further providing an exercise device for measuring the maximum muscle strength value, which includes: an exercise unit 10, a dynamically adjusted resistance unit 11 and an arithmetic control unit 12. The exercise unit 10 is used for the user to perform at least one exercise process. The dynamically adjusted resistance unit 11 is used to control changes of the resistance force during each exercise process. The arithmetic control unit 12 is signal-connected to the exercise unit 10 and the dynamically adjusted resistance unit 11, and is used to send out the resistance value that should be adjusted, and captures/accepts signals fed back by the exercise unit 10 or the dynamically adjusted resistance unit 11.

The method of this embodiment through an exercise device with dynamically variable resistance and an arithmetic control unit connected with its signal, performs the following steps: an obtaining original muscle strength value step S1, an initial muscle strength value generation step S2 and a maximum muscle strength value generation in step S3.

Wherein, the obtaining original muscle strength value step S1 is that the user performs at least one exercise process at a constant speed on the exercise device with dynamically variable resistance, and records the force value exerted by the user at each position during the exercise process, and defines force value exerted as the original muscle strength value. The exercise process described in this embodiment can be a centrifugal exercise, a centripetal exercise, or a combination of the centrifugal exercise and the centripetal exercise. In addition, the force values exerted at each position can also be marked and connected according to the position of each exercise to form an original muscle strength curve.

The initial muscle strength value generation step S2 enables the arithmetic control unit 12 to increase, decrease or remain unchanged according to the original muscle strength value of each position to generate an initial muscle strength value $W_0$. The increase and decrease described here means that the initial muscle strength value $W_0$ is obtained by calculating the original muscle strength value of each position in an equal amount, equal proportion or non-linear manner. The equal amount is to increase the original muscle strength value at each position by the same amount. The above-mentioned equal proportion means that the original muscle strength values at each position are adjusted in the same proportion. The non-linear manner refers to the reference to the relationship between process position and muscle status, and setting the increase or decrease range of each position is similar to customized adjustment of each position. To further refine the explanation, it can be regarded as an overall adjustment based on the original muscle strength curve. The adjustment method is equal amount, equal proportion or non-linear selection.

The maximum muscle strength value generation step S3: makes the exercise device with dynamically variable resistance perform an exercise test after receiving the initial muscle strength value $W_0$, performs several exercise processes during the exercise test, and the initial muscle strength value $W_0$ is gradually increased in each process. The initial muscle strength value $W_0$ after being increased is defined as a test muscle strength value $W_1$. The test muscle strength value after n times of increase is $W_n$. After completing the specified condition of the exercise test, the highest test muscle strength value reached at each position during the exercise test is the maximum muscle strength value $W_{MAX}$ of that position. The specified condition is to start the exercise test with the initial muscle strength value, and after each exercise process or several exercise processes, the test muscle strength value Wn is increased at each position by a certain value or an equal proportion manner. When the user is unable to complete the n+1th exercise process, the test muscle strength value $W_n$ during the nth exercise process is the maximum muscle strength value $W_{MAX}$ at each position.

The embodiment of the present invention further provides another maximum muscle strength value generation step S3, which performs an exercise test by the exercise device with dynamically variable resistance after receiving the initial muscle strength value $W_0$. During the exercise test, a test muscle strength value $W_1$ greater than or equal to the initial muscle strength value $W_0$ is performed; after completing the specified condition of the exercise test, the maximum muscle strength value $W_{MAX}$ is obtained according to a conversion formula. The specified condition can also be to use a certain initial muscle strength value $W_0$ as the test muscle strength value $W_1$ to perform a plurality of exercise processes, continue to exercise between each exercise process until the user no longer performs it, accumulate the user no longer performs the accumulated number of exercise processes Y, and the maximum muscle strength value $W_{MAX}=Y \times W_1/(1+(1-Y) \times c)$. Y is the accumulated number of exercise processes before the user no longer performs the action, $W_1$ is the certain initial muscle strength value, and c is a constant and between 0.01-0.1, which will vary according to different muscle groups and races, wherein one common value is 0.0278.

Taking a single position as an example, when the user completes 8 exercise processes with 10 kilograms, and the constant is 0.0278, the calculated maximum muscle strength value $W_{MAX}=W_1/(1+(1-Y) \times c)=10/(1+(1-8) \times 0.0278)=12.41619071$ kg. That is, the muscle strength curve at this position is 10 kilograms. An increase of 1.241619071 times is the maximum muscle strength curve. By the maximum muscle strength curve, the maximum muscle strength value at each position is calculated.

The present invention provides another maximum muscle strength value generation step. Wherein, the exercise device with dynamically variable resistance performs an exercise test after receiving the initial muscle strength value $W_0$. During the exercise test, it performs a plurality of test muscle strength values $W_1$ that are greater than or equal to the initial muscle strength value; after completing the specified condition of the exercise test, the maximum muscle strength value is obtained according to a conversion formula. The specified condition is to start the exercise test with the initial muscle strength value, and in each exercise process, the test muscle strength value $W_1$ of each position is increased by a certain value or an equal proportion. At this time, the conversion formula for the maximum muscle strength value at each position is:

$$W_{MAX} = W_1/(1+(1-n) \times c) + (W_2 - W_1)/(1+(1-n+1) \times c) + \ldots (W_n - W_{n-1})/(1+(1-n+n-1) \times c)$$

Wherein, $W_1$ is the test muscle strength value for the first time, $W_2$ refers to the test muscle strength value for the second time. $W_n$ refers to the nth test muscle strength value, and c is a constant and between 0.01-0.1, which will vary according to different muscle groups and races, wherein one common value is 0.0278.

For example, if the user completes three exercise tests with the muscle strength curve of $W_1=10$ kg, $W_2=15$ kg, and $W_3=18$ kg, the momentum accumulation is calculated as follows:

$$10/(1 - 2 \times 0.0278) + 5/(1 - 1 \times 0.0278) + 3/1 = 18.73173$$

It can be seen from this that the maximum muscle strength curve is the weight of the muscle strength curve of 10 kg is increased by 1.873173 times in equal proportion, which is the maximum muscle strength curve.

Through the above method, the maximum muscle strength value at each position in each exercise process can be obtained, which is not the conventional single maximum value in the exercise process. Moreover, the maximum muscle strength value is obtained through this embodiment as a reference value for dynamic adjustment, it has the function of improving training effects.

Figure 3:
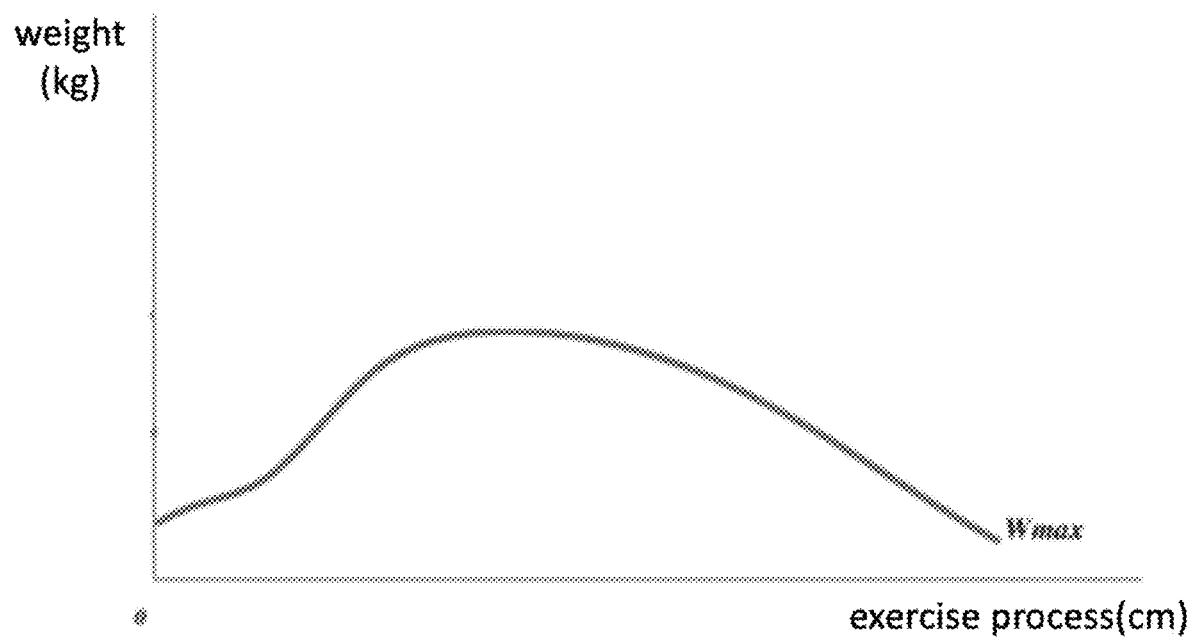
FIG. 3 is a graph of the maximum muscle force combined with the exercise process position according to the embodiment of the present invention.

This embodiment is a method that can measure the maximum muscle strength value. The maximum muscle strength value obtained by this method is along with the position of the exercise process. Therefore, if the exercise process positions and the maximum muscle strength value form coordinate values, a maximum muscle strength curve can be formed, as shown in FIG. 3. The embodiment of the present invention also introduces the application of muscle strength curve, so that the calculation of maximum muscle strength can more economize time. In the future, in addition to guiding the control of equipment output force training through the maximum muscle strength curve, it can also be used to prevent muscle injuries or for rehabilitation treatment.

In the embodiment of the present invention, the method for increasing the initial muscle strength value is to increase the test muscle strength value in an equal proportion, equal difference, certain value or non-linear manner at each position in an exercise process.

The present invention further provides an exercise device for measuring maximum muscle strength, which includes: an exercise unit, a dynamically adjusted resistance unit and an arithmetic control unit. The exercise unit is used for the user to perform at least one exercise process. The dynamically adjusted resistance unit is used to control the resistance during each exercise process. The arithmetic control unit is signal-connected to the exercise unit and the dynamically adjusted resistance unit to execute the aforementioned method to calculate the maximum muscle strength value. In addition to measuring maximum muscle strength, this device can also be used to control the dynamically adjusted resistance unit corresponding to the output for the user performing the fitness training.

The present invention further provides a kind of software for measuring the maximum muscle strength value, which can be installed in an arithmetic control unit. The arithmetic control unit is signal-connected to an exercise device with dynamically variable resistance. After executing the aforementioned method, the maximum muscle strength value is obtained. The maximum muscle strength value obtained can also be transmitted to the arithmetic control unit to control the exercise device with dynamically variable resistance, corresponding to the maximum muscle strength curve, output resistance according to the position, and providing the user with a better fitness experience.

As can be known from this embodiment, the present invention overcomes the shortcoming of the conventional technology that can only obtain a single data during the exercise process. Moreover, when the data obtained by this method is used in fitness training, the training effect can be effectively improved, and muscle injuries caused by overloading is avoided.

REFERENCE SIGNS LIST

最大肌力數值 maximum muscle strength value
運動行程 exercise process
S1 obtaining original muscle strength value step
S2 initial muscle strength value generation step
S3 maximum muscle strength value generation step
W0 initial muscle strength value
Wn., W1 test muscle strength value
WMAX maximum muscle strength value
肌力曲線 muscle strength curve
原始肌力曲線 original muscle strength curve
最大肌力曲線 maximum muscle strength curve
10 exercise unit
11 dynamically adjusted resistance unit
12 arithmetic control unit

What is claimed is:

1. A method for measuring maximum muscle strength value, which through an exercise device with dynamically variable resistance and an arithmetic control unit connected via a signal to the exercise device, performing the following steps:

an obtaining an original muscle strength value generation step, a user performing at least one exercise process at a constant speed on the exercise device with dynamically variable resistance, and recording force values exerted by the user at each position in the exercise process, and defining force values exerted as the original muscle strength value;

an initial muscle strength value generation step, the arithmetic control unit increasing, decreasing or remain unchanged based on the original muscle strength value of each position to generate an initial muscle strength value for each position; and a maximum muscle strength value generation step, after receiving the initial muscle strength value, the exercise device with dynamically variable resistance performing an exercise test, during the exercise test, using a test muscle strength value that is greater than or equal to the initial muscle strength value; after completing the specified conditions of the exercise test, obtaining the maximum muscle strength value according to a conversion formula, wherein a period of the exercise test comprises a plurality of exercise processes, and the exercise process comprises a combination of a single eccentric exercise and a single centripetal exercise, the single eccentric exercise or the single centripetal exercise; and wherein, a specified condition is to perform a plurality of exercise processes with a certain initial muscle strength value, and not stop between each exercise process until the user no longer performs each exercise process, and the number of exercise processes is accumulated before the user no longer performing, the maximum muscle strength value is equal to $W_1/(1+(1-Y)\times c)$, where Y is the number of exercise processes accumulated before the user no longer performing, $W_1$ is a certain initial muscle strength value, c is a constant and between 0.01-0.1.

2. A method for measuring maximum muscle strength value, which through an exercise device with dynamically variable resistance and an arithmetic control unit connected via a signal to the exercise device, performing the following steps:

an obtaining the original muscle strength value generation step, a user performing at least one exercise process at a constant speed on the exercise device with dynamically variable resistance, and recording the force values exerted by the user at each position in the exercise process, and defining the force values exerted as the original muscle strength value;

an initial muscle strength value generation step, the arithmetic control unit increasing, decreasing or remain unchanged based on the original muscle strength value of each position to generate an initial muscle strength value for each position; and a maximum muscle strength value generation step, after receiving the initial muscle strength value, the exercise device with dynamically variable resistance performing an exercise test, during the exercise test, using a plurality of test muscle strength values that is greater than or equal to the initial muscle strength value; after completing the specified conditions of the exercise test, obtaining the maximum muscle strength value according to a conversion formula, wherein a period of the exercise test comprises a plurality of exercise processes, and the exercise process comprises a combination of a single eccentric exercise and a single centripetal exercise, the single eccentric exercise or the single centripetal exercise; and wherein, a specified condition is to start the exercise test with the initial muscle strength value, and in the next exercise process, the test muscle strength value of each position by a certain value or an equal proportion is increased, at this time, the conversion formula for the maximum muscle strength value at each position is:

$$W_1/(1+(1-n) \times c) + (W_2 - W_1)/(1+(1-n+1) \times c) + \ldots (W_n - W_{n-1})/(1+(1-n+n-1) \times c)$$

wherein, $W_1$ is the muscle strength value of the first test, $W_2$ refers to the muscle strength value of the second test, $W_n$ refers to the muscle strength value of the nth test, and c is a constant and between 0.01-0.1.

* * * * *